United States Patent
Li

(10) Patent No.: US 10,344,238 B2
(45) Date of Patent: Jul. 9, 2019

(54) COAL AND OIL CO-HYDROTREATING PROCESSING TECHNOLOGY AND EQUIPMENT

(71) Applicant: CATECH TECHNOLOGY CO., LTD., Beijing (CN)

(72) Inventor: Suan Li, Beijing (CN)

(73) Assignee: CATECH TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/549,218

(22) PCT Filed: Feb. 4, 2016

(86) PCT No.: PCT/CN2016/073512
§ 371 (c)(1),
(2) Date: Aug. 7, 2017

(87) PCT Pub. No.: WO2016/124148
PCT Pub. Date: Aug. 11, 2016

(65) Prior Publication Data
US 2018/0023014 A1 Jan. 25, 2018

(30) Foreign Application Priority Data

Feb. 6, 2015 (CN) .......................... 2015 1 0063602
Feb. 2, 2016 (CN) .......................... 2016 1 0073074

(51) Int. Cl.
*C10G 1/06* (2006.01)
*C10G 1/08* (2006.01)
(Continued)

(52) U.S. Cl.
CPC .................. *C10L 9/04* (2013.01); *C10G 1/06* (2013.01); *C10G 1/08* (2013.01); *C10G 45/02* (2013.01);
(Continued)

(58) Field of Classification Search
CPC ..... C10L 9/04; C10L 3/08; C10L 9/06; C10G 1/06; B01D 3/14; C07C 1/0415
See application file for complete search history.

(56) References Cited

U.S. PATENT DOCUMENTS

2009/0107881 A1* 4/2009 Lott ..................... C10G 1/002
208/74
2013/0146508 A1* 6/2013 Quignard ............... C10G 1/006
208/413

FOREIGN PATENT DOCUMENTS

CN  101220287 A  7/2008
CN  103074103 A  5/2013
(Continued)

*Primary Examiner* — Randy Boyer
*Assistant Examiner* — Juan C Valencia
(74) *Attorney, Agent, or Firm* — Stuart H. Mayer; Mayer & Williams PC

(57) ABSTRACT

An oil-coal co-hydrotreating processing includes the following steps: pulverized coal, vacuum residue and recycle oil are mixed to prepare coal slurry. After mixed with hydrogen, catalyst and additive, oil-coal slurry is preheated into a slurry bed reactor with high reacting pressure for thermal cracking and hydrogenation reaction. After reaction, all the products go into the hot high pressure separator for separation of solid from the bottom and gas from the top. The gas obtained goes into the fixed bed reactor for further hydrocracking or refining, and the distillate obtained enter the fractionating tower. The vacuum gas oil from the bottom of fractionating tower is taken as recycle oil piped to the oil-coal slurry mixing device as solvent.

8 Claims, 1 Drawing Sheet

(51) Int. Cl.
*C10G 67/00* (2006.01)
*C10L 9/04* (2006.01)
*C10L 3/08* (2006.01)
*C10L 9/06* (2006.01)
*C10G 45/02* (2006.01)
*C10G 45/16* (2006.01)
*B01L 3/14* (2006.01)
*C07C 1/04* (2006.01)

(52) U.S. Cl.
CPC ............ *C10G 45/16* (2013.01); *C10G 67/00* (2013.01); *C10L 3/08* (2013.01); *C10L 9/06* (2013.01); *B01L 3/14* (2013.01); *C07C 1/0415* (2013.01); *C10G 2300/1033* (2013.01); *C10G 2300/202* (2013.01); *C10G 2300/205* (2013.01); *C10G 2300/206* (2013.01)

(56) References Cited

FOREIGN PATENT DOCUMENTS

| | | |
|---|---|---|
| CN | 104017601 A | 9/2014 |
| CN | 104629798 A | 5/2015 |
| JP | S573888 A | 1/1982 |

\* cited by examiner

COAL AND OIL CO-HYDROTREATING PROCESSING TECHNOLOGY AND EQUIPMENT

FIELD OF THE INVENTION

The invention relates to an oil and coal slurry bed co-hydrotreating technology, belonging to the field of crude oil deep processing and coal to oil production.

BACKGROUND OF THE INVENTION

China is coal-rich and oil-lean, so coal liquefaction not only has great environmental significance, but also has the strategic significance of energy security in response to today's contradiction between supply and demand and implementing the policy of energy saving and emission reduction. Further understanding of the coal resources, comprehensive utilization of coal resources and petroleum resources, and construction of integrated development model for petroleum chemical industry and coal chemical industry, are effective measures to realize the sustainable development of the petrochemical industry, to improve the efficiency of resource use and to promote resource security.

Oil-coal co-hydrotreating processing has the following characteristics: (1) High conversion: the conversion of oil-coal co-processing is more than 90%, far greater than the conversion of a single coal hydro-liquefaction or heavy oil hydrocracking. (2) Existing a synergistic effect: Due to the existence of synergistic effect between coal and heavy oil, the total amount of generated oil from oil-coal co-processing is higher than that of a single coal hydro-liquefaction or heavy oil hydrocracking, and the presence of coal not only prevents the catalyst from carbon deposition but also is conducive to removal of metallic impurities from heavy oil. Thereby, the service life of the catalyst is prolonged, and the economic benefit of the enterprise is improved. (3) The high oil yield: Compared to coal liquefaction, the oil yield of production plant is greatly improved as a result of once-through operation mode. (4) The hydrogen consumption is relatively low: Compared to coal direct liquefaction, chemical hydrogen consumption is low and hydrogen utilization rate is greatly improved for oil-coal co-processing, which is beneficial to reduce energy consumption and equipment investment. (5) The pulverized coal added not only is the feedstock, but also can adsorb the resin and asphaltene and become the coke carrier to effectively prevent the coke formation in the reaction system. (6) The quality of oil is good: Compared to coal direct liquefaction, the products with higher hydrogen content and lower aromatics content and are easily processed into qualified gasoline and diesel. (7) Strong market competitiveness: Increased conversion and productivity, lower hydrogen consumption, better oil quality and other positive factors, make oil-coal co-processing lower costs in many aspects than that of direct coal liquefaction.

On the other hand, now the main problems of crude oil processing are low light oil yield and high coke formation, which leads to poor utilization and efficiency of crude oil. Especially China's imported crude oil is mostly heavy oil with higher sulfur content, which will produce average 30% coke in the oil refining process. Many local refineries directly import heavy oil from abroad for processing, while the processing technologies of heavy oil has a large room to improve.

As a result, oil refining enterprises solve the problems of heavy oil upgrading by using oil-coal co-processing technology, and moreover, oil-coal co-processing greatly improves the light oil yield and the economic efficiency of enterprises.

Oil and coal slurry bed hydrotreating technology is a kind of coal to oil technology based on heavy oil hydrocracking process in petroleum industry. In oil-coal co-processing, coal slurry made of pulverized coal and heavy oil is hydrotreated in high temperature and high pressure to produce liquid fuel oil. Because coal has the characteristic of "aromatic rich and hydrogen deficient" while "aromatic deficient and hydrogen rich" for heavy oil and residual oil, by adjusting the co-processing conditions, it can greatly reduce the severity of direct coal liquefaction process.

At present, the domestic oil-coal co-processing mainly comprises the following steps: (1) Pulping for coal, catalyst and heavy oil; (2) Coal slurry is preheated into the reactor; (3) The reaction products are separated into gaseous substance, light oil, water and heavy mixture. Gaseous substance is purified through pressure swing adsorption by PSA for purified hydrogen that is back to reactor for recycle utilization, and the remaining gas is purified and used as fuel. Separated light oil and water are further carried on oil-water separation to get purer light oil and water; (4) A mixture of heavy oil is sent to the distillation tower to get crude oil and bottom product; (5) The mixed crude oil and light oil are upgraded to gasoline, kerosene, diesel oil, fuel oil and other liquid fuels; (6) The bottom product is processed into asphalt paving materials. The technique is combined the "aromatic rich and hydrogen deficient" coal, "aromatic deficient and hydrogen rich" residue with catalysts. By adjusting the co-processing conditions, it greatly reduces the severity of direct coal liquefaction process and produces liquid fuel and asphalt paving materials. To a certain degree, it improves the economy of direct liquefaction of coal.

There are two sections of oil-coal co-processing in abroad. Coal slurry made by heavy oil and coal with the ratio of 1:2 to 11:9 are preheated with hydrogen into a ebullated bed reactor to 435-445° C. and 15-20 MPa in the presence of Co—Mo/$Al_2O_3$ catalyst for hydrocracking reaction, and the reaction products entere the second period of ebullated bed reactor in the presence of Ni—Mo/$Al_2O_3$ catalysts for hydrogenation to removal of sulfur, nitrogen, oxygen and heavy metals (Ni, V). The gas is obtained after separating from the product, and ammonia and sulfur in the gas are recovered and then the hydrogen is recycle used. Liquid products enter atmosphere distillation and vacuum distillation to obtain target products. The process has the characteristics of simple process, reliable technology, wide range of raw material adaptation, high oil yield, high rate of metal removal of the heavy oil, etc. The technology has less hydrogen consumption and higher hydrogen utilization rate because of with no ash removal section.

But the above oil-coal co-processing will inevitably encounter such a problem: because of high viscosity of heavy oil as solvent oil, in order to ensure good stability and liquidity of coal slurry, it usually needs to reduce solid content of coal slurry. The reduction of solid content of coal slurry will affect the liquid fuel yield, and the highest solid content can reach about 35% for existing technologies.

SUMMARY OF THE INVENTION

In order to solve the problems of high viscosity of the feedstock and high cost of the catalyst of existing oil-coal co-processing technology, the present invention provides a coal and oil co-hydrotreating process and equipment.

A oil-coal co-hydrotreating processing technology, characterized as the following steps:

First of all, pulverizing the coal and drying, wherein the pulverized coal is mixed with one or several of crude oil, atmospheric residue, vacuum residue, FCC slurry oil, deasphalted oil, vacuum gas oil, coal tar in the coal and oil mixing and pulping device to prepare oil-coal slurry. After mixed with hydrogen, catalyst and additive, the oil-coal slurry is preheated into a slurry bed reactor with reacting pressure for thermal cracking and hydrogenation reaction. The coke, asphaltene and heavy metals are adsorbed on the catalyst, additives and unreacted coal in the reaction process. After reaction, all the products go into the hot high pressure separator for separation of solid from the bottom and gas from the top, and the gas goes into the fixed bed reactor for further hydrocracking or refining. Distillates obtained enter the fractionating tower, and bottom vacuum gas oil is recycled to the coal and oil mixing and pulping device. Wherein the catalyst is a mixture of molybdate and iron, the additive is a sulfurizing reagent, and the reaction pressure in the slurry bed reactor is in the range of 17-20 MPa.

The ratio of pulverized coal and residual oil is optionally 3:97-70:30, and the ratio of the catalyst, additive and the coal slurry is 0.8-1.2:2-4:100.

The particle size range of the pulverized coal is optionally 50-200 μm.

The additive is optionally one or several of carbon disulfide, dimethyl sulfide, dimethyl disulfide, n-butyl mercaptan and sodium sulfide.

Optionally, the catalyst is prepared by spray granulation of mixed iron powder and ammonium molybdate solution wherein the particle size of the catalyst is less than 10 μm.

Optionally, the mass percent concentration of the ammonium molybdate solution is 10-50%, and the molar ratio of the effective active component molybdenum to the iron is $1/100 \sim 1/300$.

The ratio of vacuum gas oil added in the feedstock is preferably 8-20%.

The oil-coal slurry preparation process is divided into the following three steps: wetting, dispersed and swelling.

The oil-coal co-hydrotreating processing technology mentioned above is further optimized as the pulverized coal and residue are mixed in the kneading machine to make the oil-coal slurry, and then the oil-coal slurry and the catalyst are mixed by two stages to form an oil-coal slurry/catalyst mixture. The oil-coal slurry/catalyst mixture and hydrogen are heated respectively and entered the first and second reactor together, and then are sent into a separation system; the light fractions are isolated as recycle hydrogen, and the heavy fractions are fractionated into gas, distillates and coal tar by atmospheric tower and vacuum tower. The coal tar is sent out of the device after moulded. The distillates that go to the fractionating device are divided into light oil, which is sent to upgrading process device, and heavy oil, which is taken as recycle oil.

A coal and oil co-hydrotreating equipment, characterized as the oil-coal slurry conveying pipe of the coal and oil mixing and pulping device is first connected with the adding device of catalyst and additive, and then combined with hydrogen pipeline and connected with the furnace. Then the pipeline for transportation of oil-coal slurry/catalyst/additive/hydrogen mixture from the furnace is connected with the slurry bed reactor and the slurry bed reactor is connected with the hot high pressure separator and wherein the upper part of the hot high pressure separator is connected with a fixed bed reactor and the bottom is connected with the vacuum flash tower. Wherein the fixed bed is further connected to the cold high pressure separator whose top is connected with a gas purification device and bottom is connected with a fractionating tower. Wherein, there are only medium distributors arranged in the internal of the slurry bed reactor but no support plate of bed, and the inner wall is ceramic. Wherein, the vacuum gas oil from fractionation tower is connected with the coal and oil mixing and pulping device.

Wherein, the additive device is preferably located on a branch pipe of the oil-coal slurry pipeline, and a portion of the oil-coal slurry is mixed with the catalyst and the additive on the branch pipe and then connected with the main oil-coal slurry pipeline.

Wherein, the gas purification device is preferably connected to the heating furnace to recover hydrogen through a circulating gas compressor.

The technical effects of the invention are as follows:

The oil-coal co-processing technology of the invention involves "slurry bed+fixed bed" reactor process. Raw material of oil-coal slurry, additive, catalyst and hydrogen mixtures enter slurry bed reactor with increased temperature and high partial pressure of hydrogen for catalytic thermal cracking reaction. Then the coke, catalyst and additive in the reaction are separated at the bottom of the hot high pressure separator. Further hydrocracking and hydrotreating are carried out in a conventional fixed bed reactor, where naphtha, light diesel oil and vacuum gas oil are produced.

First of all, the produced vacuum gas oil is taken as recycle oil. The recycle oil as solvent will greatly reduce the oil-coal slurry viscosity, improve the oil-coal slurry fluidity, increase the hydrogen donating ability of the liquid, increase the recovery and utilization of vacuum gas oil, and increase the benefit.

Secondly, due to changes in composition, the internal of the slurry bed reactor only provides with a medium distributor but no support plate of bed, which can greatly reduce the medium pressure drop. The inner wall of the reactor develops a proprietary technology, using the ceramic tube to reduce the friction of the medium and the vessel wall, greatly reducing the wall effect of fluid, which avoids the problem that the fluid is easy to attach to the wall because of the medium viscosity. and Moreover, the reaction pressure of the reactor is moderate and the catalyst is easy to prepare and the cost is low for domestic raw material that can be used.

The invention has proved that the conversion of coal and oil can reach 90-95%, and the yield of light oil can reach 65-90%.

Figure 1:
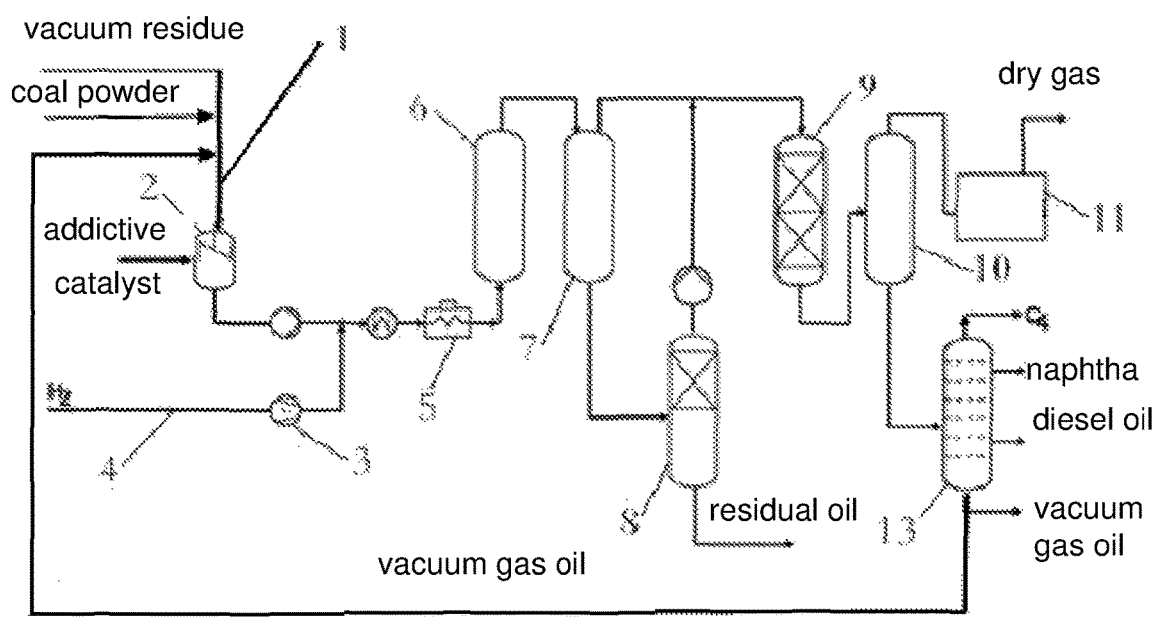
FIG. 1 is a flow diagram of example 1 of the present invention.

The reference numbers in the FIGURE are listed below:
1—oil-coal slurry pipeline, 2—adding device, 3—fresh hydrogen compressor, 4—hydrogen pipeline, 5—furnace, 6—slurry bed reactor, 7—hot high pressure separator, 8—vacuum flash tower, 9—fixed bed reactor, 10—cold high pressure separator, 11—gas purification device, 13—fractionator.

DESCRIPTION OF THE PREFERRED EMBODIMENT

Example 1

The results of this example are from a pilot test of a single oil which continuous test period of 15 days, and the device and process are shown in FIG. 1. The oil-coal slurry is made of vacuum residue (properties in Table 1), coal powder (properties in Table 2) and recycle vacuum gas oil, and is piped by the oil-coal slurry pipeline 1. Hydrogen is transported through pipeline 4 and pressurized by fresh hydrogen compressor 3. The oil-coal slurry, catalyst and additive are mixed in adding device 2 and the mixture is transported to heating furnace 5 with hydrogen injection, and the mixture goes into the slurry bed reactor 6 after increasing temperature and pressure. The additive of the example is carbon disulfide. The molar ratio of effective components of molybdenum and iron is 1:150~1:170, and the catalyst is made by spray granulation of mixed iron powder and ammonium molybdate solution to ensure the smooth surface for catalyst. The catalysts are small solid particles with sizes below 50 μm and insoluble in oil and water. The proportion of each substance follows the following basic process parameters, and the system is heterogeneous reaction. Inside the slurry bed reactor 6, there is only a medium distributor, but no support plate of bed, and the inner wall is made of ceramic.

The oil-coal slurry in the slurry bed reactor 6 under high partial pressure of hydrogen undergoes catalytic thermal cracking reaction in the presence of catalyst. The asphaltene, coke, and heavy metals in the reaction process are adsorbed on the carbon disulfide, which can ensure the long period operation of slurry bed reactor. Newly developed exclusive catalyst can make the reaction faster and overcome the shortcomings of the insufficient reaction time in the reactor caused by backmixing of residue, and can make the reaction pressure lower (see the following basic parameters) and inhibit the coke formation. Compared to other forms of reactor, pressure drop of the slurry bed reactor is lower. The inner wall of the reactor uses the ceramic tube to reduce the friction of the medium and the vessel wall which can greatly reduce the wall effect of fluid and avoid the fluid to attach to the wall and scaling problems caused by the high viscosity of the medium. Moreover, the reaction pressure of the reactor is moderate, and the catalyst is easy to prepare and the cost is low for using domestic raw material to synthesize the catalyst.

The reaction products then enter the hot high pressure separator 7. The relatively clean gas products is isolated from the top of hot high pressure separator 7, and the catalyst, additive and unreacted coal carrying asphaltene, carbon residue, sediment, metal and other solid enter the vacuum distillation tower 8 from the bottom of hot high pressure separator 7. Further hydrogenation or cracking will be taken for gas products in fixed bed reactor 9. The asphaltene, carbon residue, sediment, metal etc. are mostly removed in slurry bed reaction and separated in the bottom of hot high pressure separator 7, so they will not produce serious influence for catalyst bed of the fixed bed and it can guarantee long period operation of fixed bed reactor 9. The gas products are further processed into the cold high pressure separator 10, and the separated products are fractionated into naphtha, diesel oil, vacuum gas oil and other products in the fractionating tower 13. The vacuum gas oil in the bottom of the tower is recycled to the oil-coal slurry tank according to the amount of online oil circulation to reduce the viscosity of the oil-coal slurry. The gas enters gas purification device 11 for desulfurization, and the dry gas after purified is discharged. The property of the product is shown in table 3.

The basic process data of the present example are as follows:

TABLE 1 vacuum residue properties

| Project | Value |
|---|---|
| Density(20° C. )g/cm³ | 1.044 |
| Kinematic viscosity(mm²/s) | 2658.7 |
| Freezing point(° C.) | 45 |
| Carbon residue wt % | 24.89 |
| Ash content wt % | 0.13 |
| Acid value mg KOH/g | 1.81 |
| Components analysis wt % | |
| C | 86.79 |
| H | 10.34 |
| C/H (molar ratio) | 1.39 |
| S | 2.39 |
| N | 0.83 |
| SARA analysis wt % | |
| Saturates | 23.24 |
| Aromatics | 39.5 |
| Resin | 24.61 |
| Asphaltene | 12.59 |
| Heavy metals wt μg/g | |
| Ni | 108.2 |
| V | 402 |
| Na | 33.1 |
| Mg | 14.2 |
| Cu | 0.25 |

TABLE 2

Pulverized coal properties

| Project | Unit | Value |
|---|---|---|
| Industrial analysis | % | |
| air-dried moisture | Mad | 19.56 |
| Air as received basis | Aar | 11.22 |
| Air dried basis | Ad | 17.03 |
| Volatile matter on dry basis | Vd | 36.07 |
| Volatile matter on dry ash-free basis | Vdaf | 43.47 |
| Fixed carbon on dried basis | FCd | 46.93 |
| Calorific value | MJ/Kg | |
| Gross calorific value as dried basis | Qgr, d | 21.8 |
| Gross calorific value as dry ash-free basis | Qgr, daf | 26.3 |
| Net calorific value as air dried basis | Qnet, ad | 17.9 |
| Net calorific value as received basis | Qnet, ar | 14.4 |
| Element analysis | % | |
| Carbon content as received basis | Car | 39.71 |
| Carbon content as dried basis | Cd | 60.26 |
| Carbon content as dry ash-free basis | Cdaf | 72.62 |
| Hydrogen content as received basis | Har | 2.59 |
| Hydrogen content as dried basis | Hd | 3.93 |
| Hydrogen content as dry ash-free basis | Hdaf | 4.74 |
| Nitrogen content as received basis | Nar | 0.62 |
| Nitrogen content as dried basis | Nd | 0.94 |
| Nitrogen content as dry ash-free basis | Ndaf | 1.13 |
| Total sulfur content as received basis | St, ar | 1 |
| Sulfur content as dried basis | Sd | 1.52 |
| Sulfur content as dry ash-free basis | Sdaf | |
| Oxygen content as received basis | Oar | 10.79 |
| Oxygen content as dried basis | Od | 16.37 |
| Oxygen content as dry ash-free basis | Odaf | |
| Hardgrove grind ability index | HGI | 50 |

TABLE 3

| Product properties | |
| --- | --- |
| Light gas | 12.8% |
| Light oil | 78.9% |
| Residue slurry | 12.3% |
| Total(100 + Hydrogen consumption) | 104.0% |

In the present example, the basic technological parameters of slurry bed in pilot test are presented:

Temperature: 440-460° C.;
Experimental pressure: 17-18 Mpa;
Hydrogen to feed ratio: 1000:1~1400:1;
Space velocity: 0.5 $h^{-1}$;
Mass quality ratio of oil/coal: 30:70
The total mss quality of the recycle vacuum gas oil is 8%;
The catalyst/feed coal slurry (WT): 1/100;
Vulcanizing/feed coal slurry (WT): 2.5/100;
Chemical hydrogen consumption (hydrogen/feed) in slurry bed: 4/100 (WT).

Example 2

The operation flow of the example is roughly the same as example 1, and the difference is that the mass ratio of the oil to the coal in the feed is changed to 50:50.

The residue and the coal of the present example 2 is in accordance with example 1, and the catalytic active components of iron-molybdenum are within the ratio of 1:170~1:200 with the size less than 50 μm by spray granulation.

The basic technological parameters of the slurry bed are described in the present example:

Temperature: 450-470° C.;
Experimental pressure: 18-20 Mpa;
Hydrogen to oil ratio: 900:1~1200:1;
Space velocity: 0.6 $h^{-1}$;
Mass quality ratio of oil/coal: 50:50;
The ratio of recycle vacuum gas oil to total feed: 20%;
Catalyst/feed residue: 1.0/100 (WT);
Vulcanizing agent/feed residue: 3.5/100 (WT);
Chemical hydrogen consumption (hydrogen/feed) in slurry bed: 2.8-4.1/100 (WT) (WT).

The properties of the product of this example is shown in table 4.

TABLE 4

| Product properties | |
| --- | --- |
| Light gas | 14.7% |
| Light oil | 75.2% |
| Residue slurry | 14.5% |
| Total(100 + Hydrogen consumption) | 104.4% |

It can be seen through the above examples that high light oil yield can be obtained in low pressure environment by this technical improvement. Especially, the increase of solid content, can significantly save costs, improve efficiency, and can make great contributions for the nation to face tighter supplies of crude oil and energy saving.

The above are only preferred embodiments of the present invention, but the scope of the invention is not limited to them. Any change or replacement which can be easily thought by a person skilled in this art such as the proportion of each component in the reasonable adjustment range or something else, should be covered within the scope of the present invention. Therefore, the scope of the present invention shall be in accordance with the scope of protection of the claims.

I claim:

1. A process for an oil-coal co-hydrotreating process, the process comprising:
    pulverizing the coal and drying, wherein the pulverized coal is mixed with at least one of crude oil, atmospheric residue, vacuum residue, FCC slurry oil, deasphalted oil, vacuum gas oil, and coal tar, the mixing being performed in a coal and oil mixing and pulping device to prepare an oil-coal slurry;
    mixing the oil-coal slurry with hydrogen, a catalyst and an additive;
    after the mixing, preheating the oil-coal slurry and transporting the oil-coal slurry to a slurry bed reactor with a reacting pressure for thermal cracking and hydrogenation reaction such that coke, asphaltene and heavy metals are adsorbed on the catalyst, additives and unreacted coal in the reaction process;
    after reaction in the slurry bed reactor, transporting all products into a hot high pressure separator for separation of solid from a bottom of the—hot high pressure separator and gas from a top of the hot high pressure separator; and
    transporting the gas into a fixed bed reactor for further hydrocracking or refining; wherein distillate obtained from a reaction in the fixed bed reactor enters a fractionating tower, and bottom vacuum gas oil is transported to the coal and oil mixing and pulping device for recycling; wherein the catalyst is a mixture of molybdate and iron, the additive is a sulfurizing reagent, and the reaction pressure in the slurry bed reactor is in the range of 17-20 MPa.

2. The process according to claim 1, wherein a ratio of pulverized coal and residual oil is 3:97-70:30, and the ratio of the catalyst, additive and the oil-coal slurry is 0.8-1.2:2-4:100.

3. The process according to claim 1, wherein the pulverized coal has a particle size range of 50-200 μm.

4. The process according to claim 1, wherein the additive comprises at least one or more of carbon disulfide, dimethyl sulfide, dimethyl disulfide, n-butyl mercaptan and sodium sulfide.

5. The process according to claim 1 wherein the catalyst is prepared by spray granulation of mixed iron powder and ammonium molybdate solution, and wherein the catalyst has a particle size of less than 10 μm.

6. The process according to claim 5, wherein a mass percent concentration of the ammonium molybdate solution is 10-50%, and a molar ratio of an effective active component molybdenum to iron is 1/100~1/300.

7. The process according to claim 1, wherein a mass ratio of vacuum gas oil in the oil-coal slurry is 8-20%.

8. A coal and oil co-hydrotreating apparatus, comprising:
    an oil-coal slurry conveying pipe of a coal and oil mixing and pulping device;
    an adding device connected to the coil and oil mixing and pulping device for mixing an oil-coal slurry with a catalyst and additive;
    a furnace connected to the adding device and a hydrogen pipeline for preheating a an oil-coal slurry/catalyst/additive/hydrogen mixture;
    a slurry bed reactor connected to the furnace for performing a thermal cracking and hydrogenation reaction;

a hot high pressure separator connected to the slurry bed reactor;

a fixed bed reactor connected to an upper part of the hot high pressure separator;

a vacuum flash tower connected to a bottom part of the hot high pressure separator;

a cold high pressure separator connected to the fixed bed reactor, a top of the cold high pressure separator being connected with a gas purification device, and a bottom of the cold high pressure separator being connected with a fractionating tower; wherein only medium distributors are arranged internal to the slurry bed reactor but no support plate of the slurry bed reactor, the slurry bed reactor having an inner ceramic wall; the fractionation tower being connected to the coal and oil mixing and pulping device for recycling vacuum gas oil.

* * * * *